(12) United States Patent
Hino

(10) Patent No.: US 10,161,831 B2
(45) Date of Patent: Dec. 25, 2018

(54) VEHICLE SENSOR WITH A PLURALITY OF LEAD WIRES

(71) Applicant: DENSO CORPORATION, Kariya, Aichi-pref. (JP)

(72) Inventor: Satoshi Hino, Kariya (JP)

(73) Assignee: DENSO CORPORATION, Kariya (JP)

( * ) Notice: Subject to any disclaimer, the term of this patent is extended or adjusted under 35 U.S.C. 154(b) by 110 days.

(21) Appl. No.: 15/278,371

(22) Filed: Sep. 28, 2016

(65) Prior Publication Data

US 2017/0089808 A1 Mar. 30, 2017

(30) Foreign Application Priority Data

Sep. 28, 2015 (JP) .................................. 2015-190388

(51) Int. Cl.
*G01M 15/10* (2006.01)
(52) U.S. Cl.
CPC .................................. *G01M 15/102* (2013.01)
(58) Field of Classification Search
CPC ............. G01N 27/4077; G01N 27/407; G01N 27/4062; G01N 27/4078; G01N 1/00; G01N 27/4075; G01N 33/0027; G01M 15/102; G01M 15/104
See application file for complete search history.

(56) References Cited

U.S. PATENT DOCUMENTS

| | | |
|---|---|---|
| 5,874,664 A | 2/1999 | Watanabe et al. |
| 6,178,806 B1 | 1/2001 | Watanabe et al. |
| 6,258,234 B1 | 7/2001 | Watanabe et al. |
| 8,156,790 B2 * | 4/2012 | Matsuo .............. G01N 27/4062 204/424 |
| 8,291,746 B2 * | 10/2012 | Yamada ............. G01N 27/4077 73/23.31 |
| 8,413,482 B2 * | 4/2013 | Kume ................. G01N 27/4077 73/23.2 |
| 9,057,315 B2 * | 6/2015 | Frijas .................... F01N 13/008 |
| 9,354,142 B2 * | 5/2016 | Tahira ................. G01M 15/102 |
| 9,581,565 B2 * | 2/2017 | Kume .................. G01M 15/102 |
| 9,739,760 B2 * | 8/2017 | Noda .................. G01N 33/0027 |
| 9,847,592 B2 * | 12/2017 | Hino ................... H01R 13/2407 |

(Continued)

FOREIGN PATENT DOCUMENTS

| | | |
|---|---|---|
| JP | H09-178694 | 7/1997 |
| JP | 2004-125431 | 4/2004 |
| JP | 2004226173 † | 8/2004 |

(Continued)

*Primary Examiner* — Freddie Kirkland, III
(74) *Attorney, Agent, or Firm* — Nixon & Vanderhye PC

(57) ABSTRACT

A sensor for a vehicle 1 is provided with a sensor element, plurality of lead wires electrically connected to the sensor element, a metallic cylindrical cover and a rubber bush positioned in a partial inner-space of a base end of the cylindrical cover. Radial contraction of the cylindrical cover and compression of bush, deforming the bush radially inward thereof, supports the leads wires inserted through each of the respective through-holes. The cylindrical cover is provided with a curved portion having a base end of which a whole circumferential edge is bent radially inward, thereby producing the curved portion opposing a rim of the bush in an axial direction.

7 Claims, 6 Drawing Sheets

(56) References Cited

U.S. PATENT DOCUMENTS

2009/0223818 A1 * 9/2009 Matsui .............. G01N 27/4062
204/412

FOREIGN PATENT DOCUMENTS

| JP | 2008-096247 | | 4/2008 | |
|----|-------------|---|---------|---|
| JP | 2011-257198 | | 12/2011 | |
| JP | 2012233788 A | * | 11/2012 | ........... G01N 27/409 |
| JP | WO2013/128801 | | 9/2013 | |
| JP | 5529070 | † | 6/2014 | |
| JP | 2014-149181 | | 8/2014 | |
| JP | 2015-68682 | | 4/2015 | |
| WO | 2015115660 | † | 8/2015 | |

\* cited by examiner
† cited by third party

BEFORE CAULKING

AFTER CAULKING (a) BEFORE CAULKING (b) DURING CAULKING (c) AFTER CAULKING

VEHICLE SENSOR WITH A PLURALITY OF LEAD WIRES

CROSS-REFERENCE TO RELATED APPLICATION

This application is based on and claims benefit of the priority from earlier Japanese Patent Application No. 2015-190388 filed Sep. 28, 2015 the description of which are incorporated herein by reference.

BACKGROUND OF THE INVENTION

Technical Field

The present invention relates to a sensor for a vehicle, for the detection of concentration of a specific gas from an automotive engine or the like, and more particularly, to a sensor for a vehicle structurally holding a plurality of lead wires.

Related Art

Sensors for a vehicle, for example, gas sensors are provided with a section extended to an exterior in order to connect, for example, a control device, to a plurality of lead wires electrically connected to a sensor element. With the recent development of sensors for vehicles, efforts are being made to provide sensors that are protected from water droplets entering inside the sensor, to maintain both the performance of the sensor and integrity of the structure. For example, an air/fuel ratio sensor disclosed in the Japanese Patent Literature 1 discloses a protection cover that is provided with an elastic insulating member, and by caulking the protection cover inwards, an outer diameter of the elastic insulated member is radially contracted, securely fixing a seal in insertion holes of the respective lead wires, improving water resistance of the air/fuel ratio sensor.

CITATION LIST

Patent List

[Patent Literature 1]
Laid-open Patent Number H9-229897

In a situation of extending lead wires to an exterior of a sensor, a caulking section, which prevents water incursion to inside the sensor, is positioned at an end-section of a protection cover, thus, the structural-strength is low at the end-section of the protection cover. Also, since the end-section of the protection cover is positioned relatively close to the caulking section, the protection cover may be significantly deformed as a consequence. For example, if a formation around the end of the protection cover, and a formation of the caulking section are inappropriately deformed, there is risk of variation of the compression state in a circumferential direction of the caulking section. In such an event, the uneven compression state may allow water droplets to easily intrude inside the sensor, from an area where compression is low.

Furthermore, when the numbers of lead wires used are increased in accordance to the needs, a degree of compression surrounding the lead wires is not uniform, and variation of seal bearing pressure increases. At this point, the compression-level of the caulked-lead wires is high, and in turn, the seal bearing pressure increases. However, when the seal bearing pressure (i.e., pressure acting on the seal) increases, incursion of water droplets can easily occur inside the sensor, due to undesirable deformation of the protection cover caused by caulking thereof. For the reasons described, maintaining water resistance of the sensor and increasing the number of lead wires becomes difficult in this configuration. Considering that a gap between an end of the protection cover and an elastic insulation member becomes an entrance for water droplets to intrude inside the sensor, it is necessary to further devise a structure which effectively prevents the incursion of water droplets inside the sensor.

SUMMARY

An object of the present disclosure lies in providing a sensor for a vehicle in which incursion of water is effectively prevented.

An aspect of the present disclosure is a sensor for a vehicle provided with a sensor element, a plurality of lead wires electrically connected to the sensor element, and a metallic cylindrical cover provided with an inner space. The cylindrical cover has an axial direction which is along a central axis of the cylindrical cover, a radial direction which extends radially from the central axis, and a circumferential direction which is around the axial direction. The cylindrical cover has a front end and a base end in the axial direction and a rubber bush arranged in the partial inner space of the cylindrical cover in the axial direction. The partial inner space being positioned on an inner side of the cylindrical cover in the axial direction; and the rubber bush provided with a plurality of insertion holes, the plurality of lead wires being inserted through the respective insertion holes, wherein the lead wires inserted through the insertion holes are supported by radial contraction of the cylindrical cover at a portion near to a base end of the cylindrical cover.

The bush is further provided with a rim which expands radially outward, the cylindrical cover is provided with a curved portion having the base end of which the whole circumferential edge is bent radially inward, thereby producing the curved portion and opposing the rim of the bush in the axial direction.

The sensor for a vehicle is provided with the cylindrical cover and the bush, formed so that water resistance is increased. More specifically, the cylindrical cover is provided with the curved portion, curving the base end toward an inner-side thereof. In providing the curved portion, the strength of the base end of the cylindrical cover is thus increased. Also, since the bush having each of the lead wires inserted through each of the respective through-holes is positioned at an inner peripheral-side of the base end of the cylindrical cover, it becomes difficult for deformation, for example, by buckling thereof to occur, if the cylindrical cover is radially contracted to reduce a diameter thereof. As a result, inappropriate deformation of the cylindrical cover is prevented, and the contraction ability of the cylindrical cover and compression capacity of the bush to deform therein is increased. In particular, even in a situation of increasing a number of lead wires, the sealing bearing pressure of a seal can be highly maintained between the cylindrical cover and the bush, and between the through-holes and lead wires respectively.

The bush is provided with a rim opposing an exterior-side of the curved portion, in the axial direction. Additionally, a tip-end of the curved portion is covered by the rim of the bush, so that it can be difficult for water droplets to enter inside the sensor from a gap therebetween. An effect of the cylindrical cover provided with the curved portion, and an effect of the bush provided with the lid section positioned on an outer periphery of the curved portion, together enhance the structure of the sensor for a vehicle. Therefore, sealing between the curved portion and the rim of the bush restrain-

DETAILED DESCRIPTION OF THE PREFERRED EMBODIMENT

Figure 1:
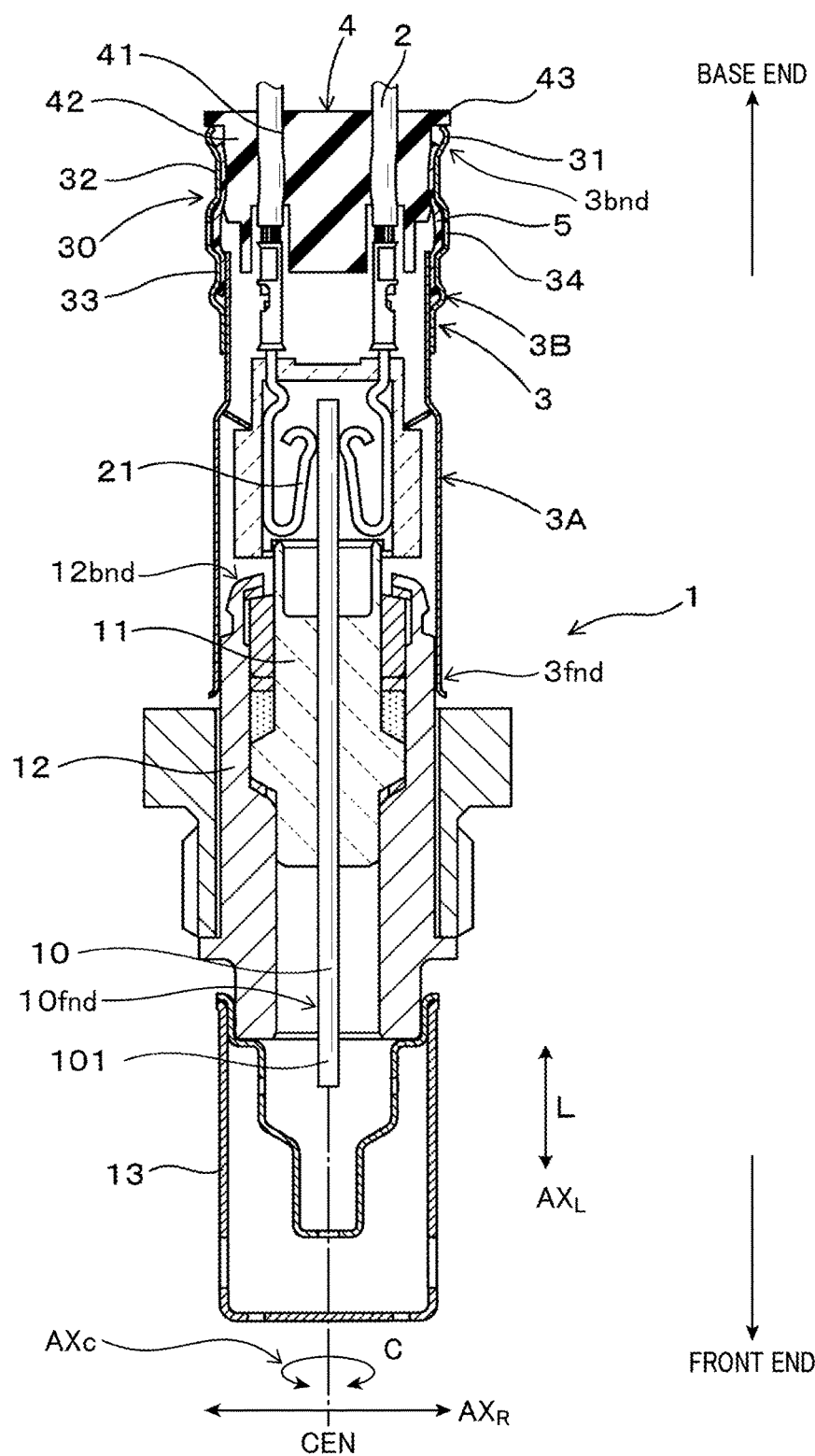
FIG. 1 shows a cross sectional view of a sensor for a vehicle according to an embodiment.

With reference to the indicated drawings, a preferred embodiment of the present disclosure will be described hereon. As shown in FIG. 1, a sensor for a vehicle 1 is provided with a sensor element 10, and a plurality of lead wires electrically connected to the sensor 10, a metallic cylindrical cover 3 and a rubber bush 4 arranged in a partial inner space 3 in being positioned on an inner side of a base end of the of the cylindrical cover 3.

The "partial inner space $3_{in}$", defines part of the cylindrical cover 3 inner space which is occupied by the bush 4. As is shown in the FIG. 1 a longitudinal direction of the cylindrical cover 3 is defined as axial longitudinal direction $AX_L$. A radial direction defined as $AX_R$ and the circumferential direction defined as $AX_C$, with respect to the $AX_L$. The rubber bush 4 is provided with a plurality of insertion holes 41 for inserting of the plurality of lead wires 2 therethrough.

Figure 3:
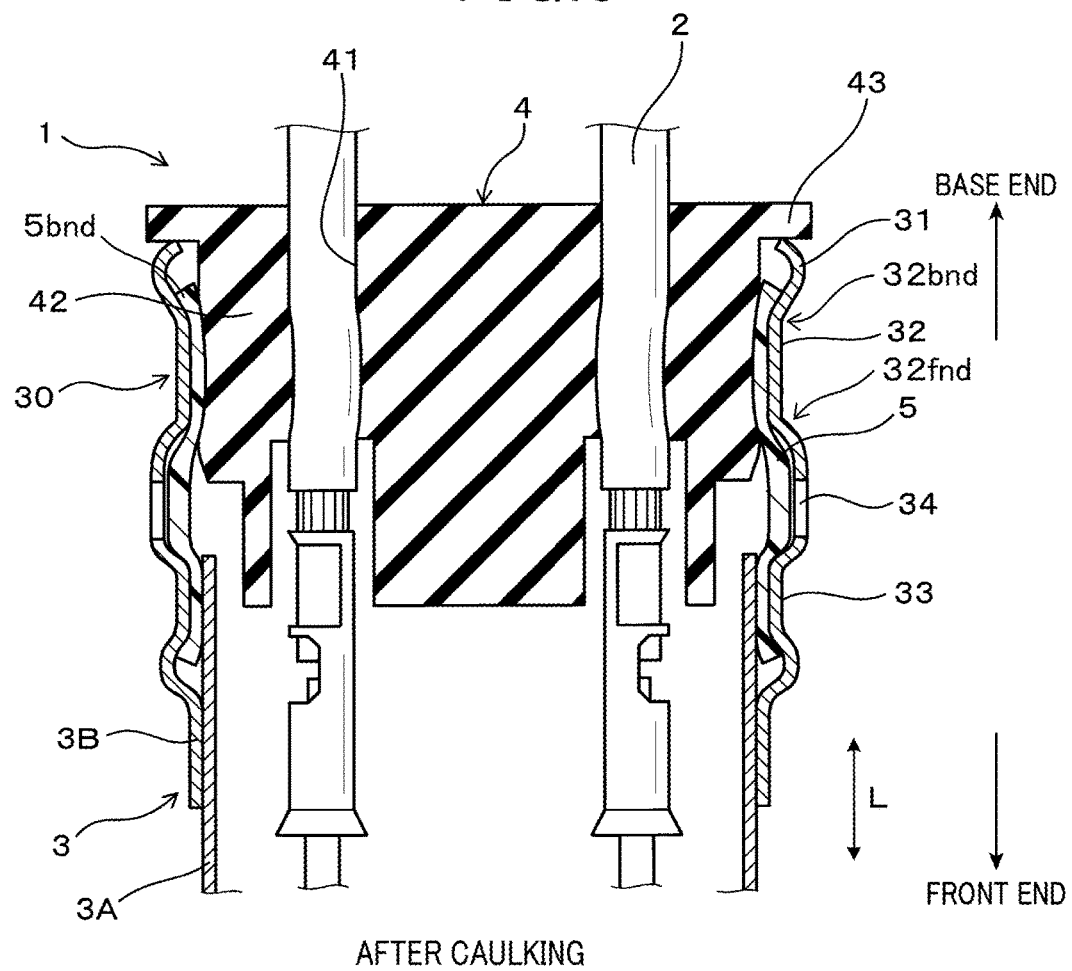
FIG. 3 is a cross sectional view showing a state of the cylindrical cover and the periphery of the bush of the sensor for a vehicle after the cylindrical cover is radially contracted according to the embodiment.

As shown in FIG. 1 and FIG. 3, the sensor 1 is configured to support each of the lead wires in each of the respective insertion holes 41, by radial contraction of the cylindrical cover 3 and compression of the bush 4 to deform thereof. That is, the bush 4 is radially compressed inwards to deform thereof. 'Deform' or 'deformation' hereon defines a change in shape thereof when pressure is applied. The cylindrical cover 3 is provided with a curved portion 31 having a base end $3_{bnd}$ of which the whole circumferential edge is bent radially inwards thereby producing the curved portion 31. The bush 4 is provided with a rim 43 opposing the curved portion 31. Hereon, 'bnd' and 'fnd' defines a 'base-end' and 'a front end' respectively, thereof, for example, '$3_{bnd}$' defines the 'base end' of the cylindrical cover 3, and '$3_{fnd}$' defines a front end of the cylindrical cover 3. It is accountable that 'base end' and 'front end' may not be precisely measured lengths, but may refer to the base or front end of a whole part, portion or section, for example.

The sensor for a vehicle 1 is disposed on a four wheeled vehicle or a two wheeled vehicle, incidentally, the sensor 1 in the preferred embodiment is a gas sensor to detect a concentration of gas. The gas sensor is mounted on an exhaust pipe of a combustion engine of an automotive engine, for example. The gas sensor detects the concentration of specific gases of an exhaust gas flowing through the exhaust pipe, such as the oxygen (O2) and nitrogen oxide (NOx) for example. With reference to FIG. 1, a sensor element 10 of the gas sensor is provided with a solid electrolyte having oxygen ion conductivity, an electrode disposed on both sides of the solid electrolyte, and a heater which heats the solid electrolyte. The electrodes include three electrodes exposed to exhaust gas and one electrode exposed to an atmosphere. The plurality of lead wires 2 include four lead wires 2, which are connected to the four electrodes through metallic fittings 21, and two lead wires 2 which are connected to both ends of a front section of a heating wire of a heater through the metallic fittings 21.

Figure 5:
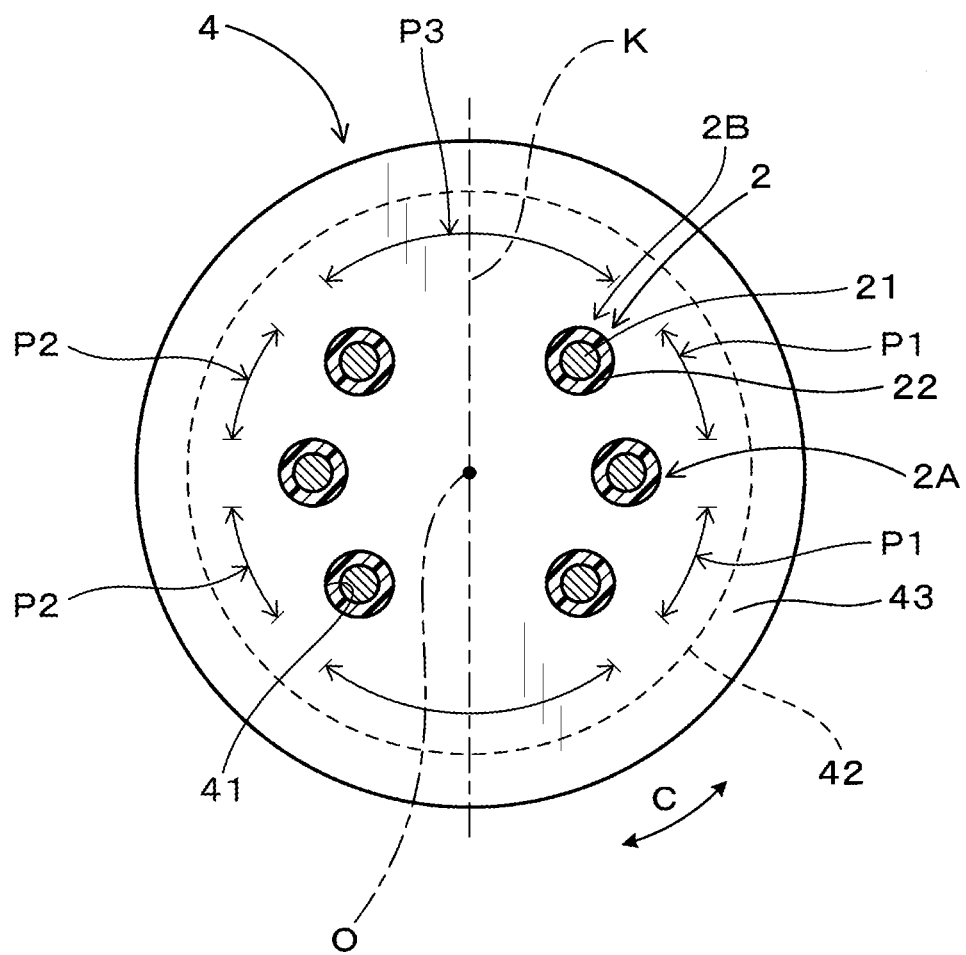
FIG. 5 is an explanatory view showing the bush and lead wires viewed in the axial direction of the sensor for the vehicle according to the embodiment.

A cross sectional view of the bush 4 in FIG. 5 shows the plurality of lead wires 2 and the plurality of through-holes 41 in which the lead wires 2 are inserted in the respective through-holes. In FIG. 5, the positions of the through-holes 42, that is, the positions of the lead wires 2 are provided with a line symmetry on a virtual line K passing the center of the bush 4. By using the virtual line K which is drawn as shown in FIG. 5, the positions of the through-holes 42 can be positioned at three positions on both left and right areas. In this configuration, the six positions are arranged in the circumferential direction C with different circumferential pitches. The pitches include, at least, one pitch which is different from the remaining pitches. For instance, as shown in FIG. 5, pitches P1, P2 and P3, which are positioned at the respective right, left and upper parts, satisfy P3≠P1 and P2. Of course, this is just an example. In the present embodiment, it is sufficient that the pitches among the positions of the through-holes 42 can be different from each other in part or entirely in the circumferential direction C.

As shown in FIG. 1, the sensor element 10 is formed as a long-shaped member with a longitudinal direction thereof parallel with an axial direction L of the cylindrical cover 3. For each of the configuring members of the sensor for a vehicle 1; a direction parallel with the cylindrical cover $3_{in}$ the axial direction 'L', is shown as 'a front end' or as a 'base end' of the axial line direction L. The sensor element 10 supports an insulator 11, and the insulator 11 is arranged in a housing 12. A sensor detection member 101 disposed on the front-end $10_{fnd}$ of the sensor element 10, in the axial direction L, protrudes from the insulator 11 and is covered by a front-end cover 13 which is attached to the housing 12. The cylindrical cover 3 is a member positioned at an outermost periphery of the sensor 1, attached to a base end $12_{bnd}$ of the housing 12, in the axial direction L. The bush 4 is positioned at the partial inner space $3_{in}$ of the base end $3_{bnd}$ of the cylindrical cover 3, in the axial direction, preventing water incursion intruding from the base end $3_{bnd}$ of the cylindrical cover 3 to an inside of the sensor for a vehicle.

Figure 2:
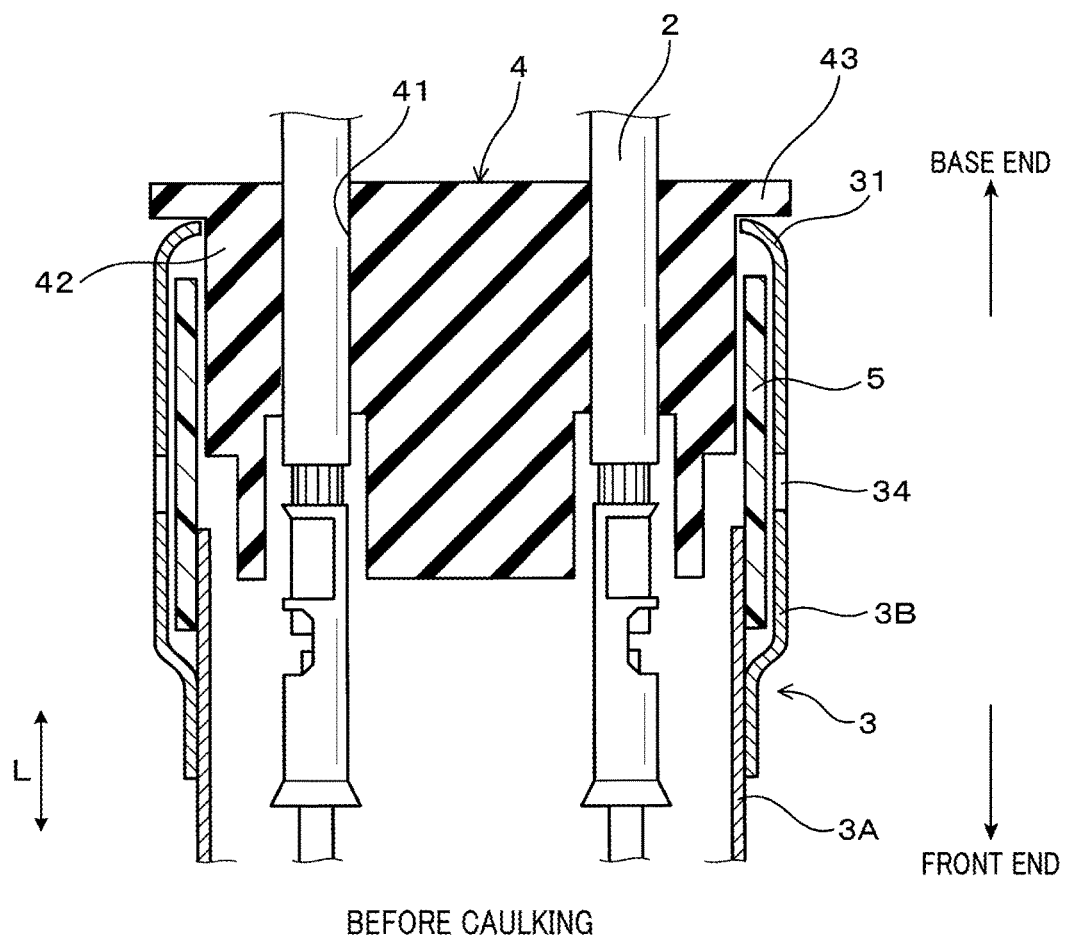
FIG. 2 is a cross sectional view showing a state of a cylindrical cover and a periphery of a bush of the sensor for a vehicle before the cylindrical cover is radially contacted according to the embodiment.

As shown in FIG. 2 and FIG. 3, a caulking section 30, a section that is provided to caulk the cylindrical cover 3 and the bush 4, is positioned adjacent to the front end of the curved portion 31, in the axial direction L. A first caulked concave section 32, having a contracted outer diameter, with respect to the outer diameter of the curved portion 31, is formed around the base end $3_{bnd}$ of the cylindrical cover 3, in the axial direction. Additionally, when the first caulked concave-section 32 is formed using a caulking tool, for example, the curved portion 31 adjacent to a base end $32_{bnd}$-side of the caulked section 32, and a section positioned at a front end $32_{fnd}$-side of the caulked section 32 in the axial-direction L, are spread outward. As a consequence, the curved portion 31 changes from a curved-state toward the inner-side thereof, to an oblique-state with respect to the axial direction L of the sensor element 10 when the curved portion 31 is projected toward the outer-side thereof.

Figure 4:
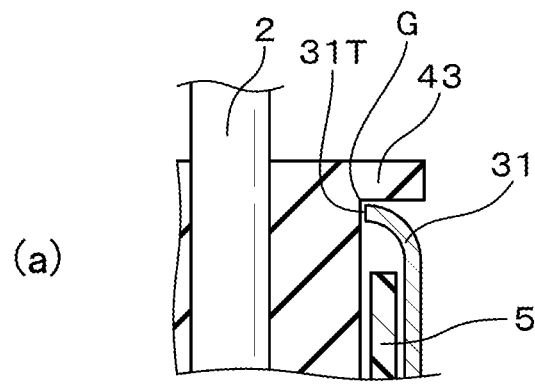
FIG. 4 is a cross sectional view showing movement of a curved portion of the cylindrical cover before caulking, during caulking and after the caulking process, respectively (from left to right) when the cylindrical cover and bush are caulked therein.
Figure 4:
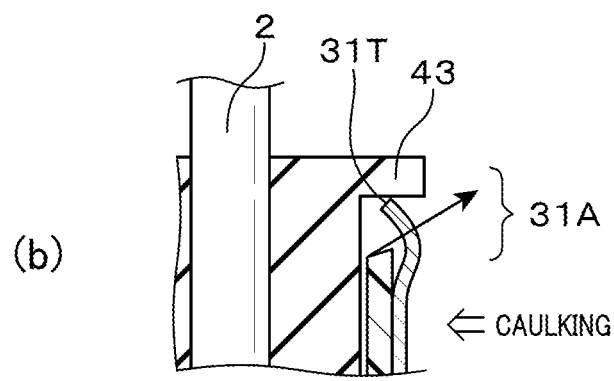
Figure 4:
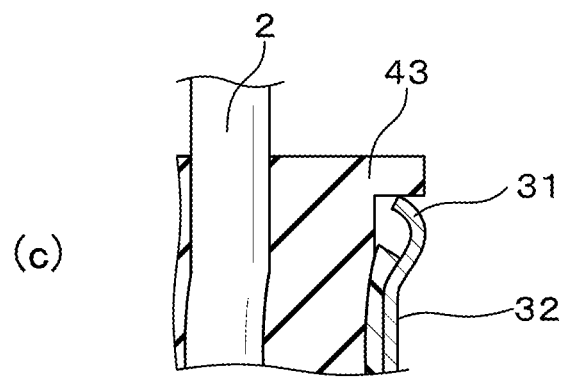

FIG. 4 illustrates a sequence of movements of the curved section 31 of the cylindrical cover 3, when the cylindrical cover 3 and bush 4 are caulked. That is, when the bush 4 is radially compressed into the partial inner space $3_{in}$ of the cylindrical cover 3. As shown in FIG. 4 (a) before caulking, a gap G is provided between the rim 43 and the tip-end 31T of the curved section 31. At the point of caulking, pressure is applied radially to the cylindrical cover 3, refer to FIG. 4 (b). At this moment, the bush 4 that is positioned at the partial inner space $3_{in}$ of the cylindrical cover 3, is compressed to deform thereof. The cylindrical cover 3 contracts inwardly so that the diameter in reduced, and at the same time the curved portion 31 deforms by curving outward, so that the tip-end 31T of the curved section 31 faces the lid 43-side, and is in contact with the rim 43. As shown in FIG. 4(c), by caulking the cylindrical cover 3 and the bush 4, the tip-end 31T of the curved portion 31 and the rim 43 of the bush 4 are substantially in contact, thus the gap G is closed off.

As is shown in FIG. 5, the lead wires 2 are composed of a conductor section, for example, a copper lead, and a lining 22 of resin which lines the periphery of the conductor 21. When the bush 4 is compressed to deform thereof, the lining 22 of the lead wires 2 is compressed, and in turn, the lining 22 of the lead wires 2 and the push through-hole 41 are closely fixed together. Each of the lead wires 2 deform thereof by radial contraction of the first caulked concave section 32, refer to FIG. 3. "Radial contraction" hereon defines a reduction of the diameter in the caulking-section 32". In this moment, the section opposing the inner periphery side of the first caulked concave section 32 is curved inwards to the inner peripheral-side.

A filter 5 having properties of preventing a liquid substance, for example water, from penetrating therethrough, and allowing a gaseous body, for example, air to pass therethrough, is sandwiched between the inner-side of the cylindrical cover 3 and an outer-side of the bush 4, refer to FIG. 3. The filter 5 is formed from a resin material having a minute fibrous structure, which allows ventilation. A through-hole 34 is formed in a position opposing the filter 5 of the cylindrical cover 3. In addition, the through-hole 34 is positioned closer to the front end, than the position of the bush 4 subjectively deformed by compression therein, in the axial direction, when the cylindrical cover is radially contracted. Incidentally, by providing the filter 5 and the through-hole 34, for example, incursion of water droplets inside the sensor for a vehicle 1 is prevented, and adjustment of airflow and pressure of the sensor for a vehicle 1 can be performed.

The cylindrical cover 3 is divided into a first cover section 3A positioned at the inner periphery thereof, which is the front end of the axial direction L, and a second cover section 3B is disposed to overlap the base end of the first cover section 3A from the outer peripheral side. A base end portion $5_{bnd}$ of the filter 5, in the axial direction L is subjected to deformation, by the contraction of the first caulked concave section 32, and is sandwiched between the bush 4 and the second cover section 3B. On the other hand, the front end portion $5_{fnd}$, in the axial direction L, of the filter 5 is subjected to deformation by contraction of a second caulked concave section 33, and is sandwiched between the first cover section 3A and the second cover section 3B.

The bush 4 is provided with a body part 42, positioned at an inner-side of the second cover section 3B of the cylindrical cover 3, and the rim 43 positioned at a base thereof, in the axial direction L, projected toward the outer peripheral side. As shown in FIG. 3 and FIG. 4, the rim 43 is in contact with a tip-end 31T of the curved portion 31, covering the curved portion 31 from the base end thereof, in the axial line direction.

As shown in FIG. 2, when assembling the gas sensor, the front end portion $3B_{fnd}$ of the second cover section 3B is fitted over an outer-side of the first cover section 3A, and at the same time the filter 5 is sandwiched between the base end portion $3A_{bnd}$ of the first cover section 3A and the second cover section 3B. The bush 4 provided with each of the lead wires 2 inserted through each of the respective through-holes 41, is positioned at the inner peripheral-side of the second cover 3B and the filter 5. With reference to FIG. 3, a base end of the second cover section 3B is radially contracted using a caulking tool, and in turn, a section of the bush 4 is compressed to deform, in order to fit in the partial inner space $3_{in}$ of the cylindrical cover 3, whereby each of the lead wires 2 are in close contact with the respective through-holes of the bush 4. In this way, the second cover 3B, the filter 5 and the bush 4 are caulked using the caulking tool, gaps therebetween are closed off, and gaps between each of the through-holes 41 and each of the lead wires 2 are also closed off. The first caulked concave section 32 is formed in a section of the second cover 3B that is caulked.

A strength of the base end of the second cover section part 3B is increased by providing the curved portion 31 which curves toward the inner-side thereof. Also, deformation, such as buckling, for example, of the second cover section 3B is restrained by the curved portion 31, when the second cover 3B is radially contracted and the second cover 3B, the filter 5 and the bush 4 are caulked therein. Specifically, since the curved portion 31 is in close contact with the rim 43 of the bush 4, not only is the strength of the base end part of the second cover 3B increased but also the second cover 3B of the cylindrical cover 3 is also supported by the rim 43 of the bush 4. As a result, inappropriate deformation of the second cover section 3B is prevented, and the contraction of the second cover section 3B and compression level for the deformation of the bush 4 can also be significantly increased. In particular, bearing pressure of the seal between the second cover section 3B and bush 4, and between the through-holes 41 of the bush 4 and the lead wires 2, can be maintained at a high value even if the number of lead wires 2 are increased.

The bush 4 is provided with the rim 43, which opposes an outer-side of the curved portion 31 of the second cover 3B. The tip-end 31T of the curved portion 31 is covered by the rim 43, and the gap between the tip-end 31T of the curved portion 31 of the second cover portion 3B and the bush 4, which is a route entrance for water to intrude inside the sensor, is blocked-off by the rim 43. As a result, in this configuration, protection from the incursion of water entering inside the sensor for a vehicle is obtained. An effect of the cylindrical cover 3 provided with the curved portion 31 at the base end thereof, and an effect of the bush 4 provided with the rim 43, positioned at the outer-side of the curved portion 31, together enhance the structure of the sensor for a vehicle 1.

Figure 6:
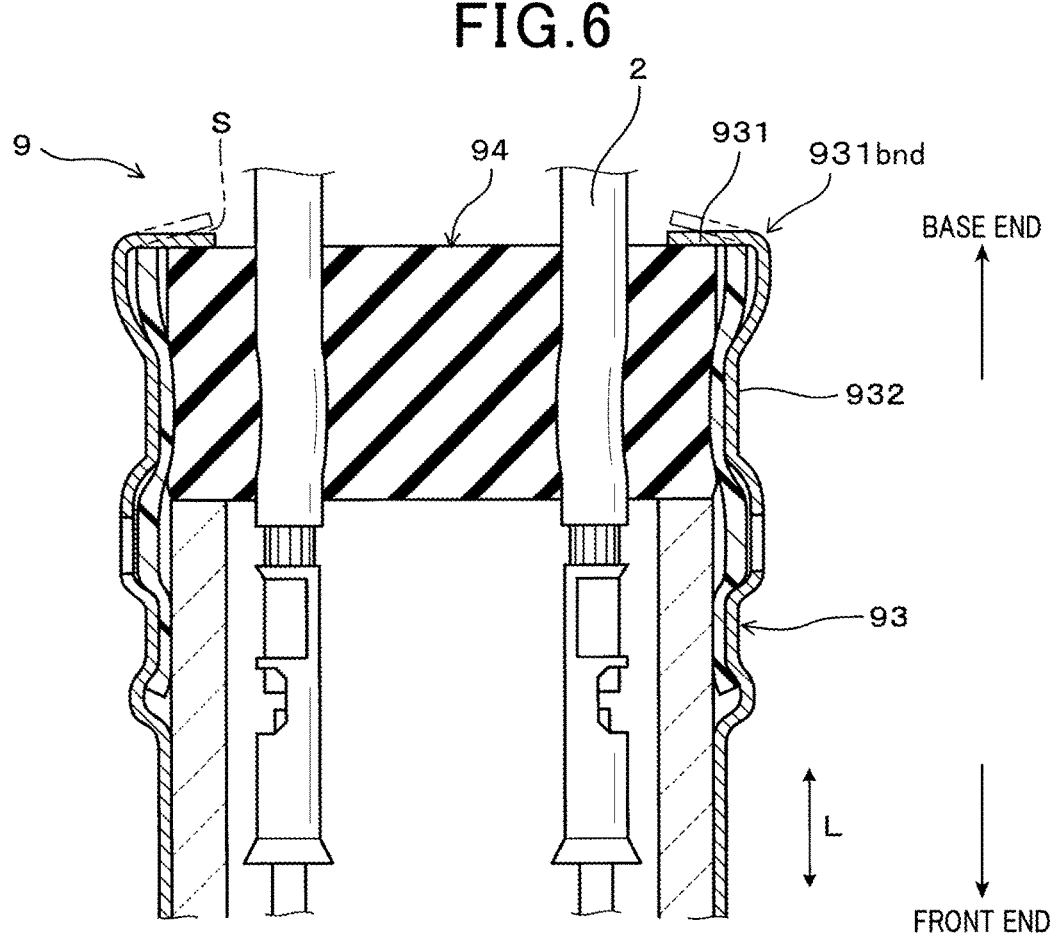
FIG. 6 is an explanatory view showing a state of a bush and lead wires of a conventional sensor for a vehicle according to the embodiment.

The benefits of the sensor for a vehicle 1 will now be described comparatively with a conventional sensor for a vehicle 9. As shown in FIG. 6, the conventional sensor for a vehicle 9 is provided with a curved portion 931, curving to an inner peripheral-side of an end-section $93_{bnd}$ of a cylindrical cover 93, positioned thereon an end which is the base end of a bush 94. Referring to the same Figure, when the cylindrical cover 93 is radially contracted, and the cylindrical cover 93 and the bush 94 fixedly caulked together, the curved portion 931 positioned adjacent to the caulked section 932 essentially deforms, that is specifically, the curved portion 931 deforms in an outward direction away from the bush 94. The deformation of the curved portion 931 is shown by the two dotted line in FIG. 6. In such a circumstance, a gap S is formed between the curved portion 931 and an end-side, that is a base end of the bush 94 and the gap S forms an entrance for water to intrude inside the sensor for a vehicle 9. The conventional sensor 9 is thus disadvantageous from the view point of water resistance and from the view point of potential rusting of the cylindrical cover 93, since the gaps formed in the configuration enable the accumulation of water between the curved portion 931 and the base end of the bush 94.

In contrast, according to the sensor for a vehicle 1 in the embodiment, when the cylindrical cover 3 is radially contracted and the cylindrical cover 3 and bush 4 caulked together, the tip-end 31T of the curved portion 31 deforms to the outer direction pressing against the rim 43 of the bush 4 as shown in FIG. 4. As a result, a sealed formation between the tip of the curved portion 31 and flexible body rim 43 can be achieved. Furthermore, intrusion of water inside the sensor for a vehicle 1 is effectively avoided, and thus the present configuration advantageous from the view point of water resistance. Since it is also difficult for water to accumulate between the tip-end 31T of the curved portion 31 and the rim 43, the sensor for the vehicle 1 is advantageous from the viewpoint of potential rusting of the cylindrical cover 3.

Additionally, the plurality of lead wires 2 are positioned in a circumferential direction of the bush 4 at pitches that are, at least, partially, different from each other in the circumferential direction. Under the circumstances, the bearing pressure around the lead wires 2 is largely dispersed due to a change in a thickness of a section of the bush 4, which is the section peripheral to the lead wires 2, and also due to the effects of a change in the interval between the adjacent lead wires 2. The 'interval change' herein refers to a distance between each of the lead wires 2. As a result, deformability thereof by caulking the cylindrical cover 3 and bush 4 is large, and sufficient bearing pressure occurring at the periphery of the lead wires 2 is secured.

In the embodiment, by devising a structure which provides the curved portion 31 disposed at the base end of the second cover section 3b, the strength of the base end thereof is increased. Also, when deformability of caulking the cylindrical cover 3 and bush 4 is increased, inappropriate deformation of the second cover 3B, such as buckling, for example which can cause creases to occur, and water incursion inside the sensor is avoided. Consequently, even in an exceptional case where the pitch having the plurality of lead wires 2 positioned in the circumferential direction of bush 4 is partially different, the bearing pressure of the seal between the second cover 3b and the bush 4, and between the through-holes 41 of the bush 4 and lead wires, can be maintained at a high level. Maintaining the bearing pressure also effectively prevents water from intruding inside the sensor 1, in the configuration described.

The sensor for a vehicle 1 is configured so that, the tip end 31T of the curved portion 31 is positioned between the rim 43 of the bush 4 and an end-section 51 of the filter 5, in the axial direction L thereof. When the bush 4 is assembled in the partial inner space $3_{in}$ of the cylindrical cover 3 and the filter 5, the tip-end 5T of the filter 5 is covered by the tip end 31T of the curved portion 31. As a result, the rim 43 of the bush 4 is always secured by the tip-end 31T of the curved portion 31, and an application of pressure to the tip end 5T of the filter 5 by the bush 4 is avoided, when the bush is assembled. That is, during the assembling process, the structure of the filter can be maintained. The filter 5 is formed from a resin having a minute fibrous structure to allow air to pass through a plurality of minute pores formed therein. As the filter 5 is formed from the resin material, in a situation of pressing or applying pressure in a direction along a surface thereof, the plurality of pores will be closed off, which in turn may prevent a flow of air passing therethrough, resulting in a loss of the air-flow.

Since the sensor for a vehicle 1 is structured so that the tip-end 31T of the curved portion 31 firmly supports the rim section 43 of the bush 4, compression or pressure in a direction along the surface of the filter 5 will not occur, thus, a flow of air therethrough can be securely maintained. Thus ventilation of the sensor for a vehicle can be maintained even if assembly precision of the bush 4 at a point of assembling thereof is not strictly managed.

What is claimed is:
1. A sensor for a vehicle, comprising:
a sensor element;
a plurality of lead wires electrically connected to the sensor element;
a metallic cylindrical cover provided with an inner space; the cylindrical cover having an axial direction which is along a central axis of the cylindrical cover, a radial direction which extends radially from the central axis, and a circumferential direction which is around the axial direction, the cylindrical cover having a front end and a base end in the axial direction;
a rubber bush arranged in a partial inner space of the cylindrical cover in the axial direction, the partial inner space being positioned on an inner side of the cylindrical cover in the axial direction; and the rubber bush being provided with a plurality of insertion holes, the plurality of lead wires being inserted through the respective insertion holes; and
a filter having a front end portion and a base end portion in the axial direction, wherein:
the lead wires inserted through the insertion holes are supported by radial contraction of the cylindrical cover at a portion close to a base end of the cylindrical cover,
the bush is further provided with a rim which expands radially outward in the radial direction, and
the cylindrical cover is provided with a curved portion at the base end of the cylindrical cover, the curved portion being a whole circumferential edge that is bent radially inward in the radial direction, thereby producing the curved portion and the curved portion having a tip-end positioned between the rim of the bush and the base end portion of the filter in the axial direction, such that the curved portion opposes the trim of the bush and the rim of the bush is in contact with the tip-end.
2. The sensor according to claim 1, wherein the plurality of lead wires are positioned at pitches in a plane crossing the axial direction, the pitches including two or more pitches different from each other in the circumferential direction, and the plane being along an upper surface of the bush.

3. The sensor of a vehicle according to claim 2, wherein:
the filter having properties of not allowing a liquid to pass therethrough and allowing a gas to pass therethrough, the filter being sandwiched between the cylinder cover and the bush; and
a ventilation-hole formed in a position opposing the filter.

4. The sensor for a vehicle according to claim 2, wherein the sensor element detects an electric signal corresponding to an exhaust concentration.

5. The sensor of a vehicle according to claim 1, wherein:
the filter has properties of not allowing a liquid to pass therethrough and allowing a gas to pass therethrough, the filter being interposed between the cylinder cover and the bush; and
a ventilation-hole formed in a position opposing the filter.

6. The sensor for a vehicle according to claim 5, wherein the sensor element detects an electric signal corresponding to an exhaust concentration.

7. The sensor for a vehicle according to claim 1, wherein the sensor element detects an electric signal corresponding to an exhaust concentration.

\* \* \* \* \*